(12) United States Patent
Sawada et al.

(10) Patent No.: US 11,492,593 B2
(45) Date of Patent: Nov. 8, 2022

(54) METHOD FOR PURIFICATION OF RETINAL PIGMENT EPITHELIAL CELLS

(71) Applicants: HEALIOS K.K., Tokyo (JP); OSAKA UNIVERSITY, Suita (JP)

(72) Inventors: Masanori Sawada, Tokyo (JP); Kiyotoshi Sekiguchi, Suita (JP)

(73) Assignees: HEALIOS K.K., Tokyo (JP); OSAKA UNIVERSITY, Suita (JP)

( * ) Notice: Subject to any disclaimer, the term of this patent is extended or adjusted under 35 U.S.C. 154(b) by 0 days.

(21) Appl. No.: 15/028,158

(22) PCT Filed: Oct. 9, 2014

(86) PCT No.: PCT/JP2014/077112
§ 371 (c)(1),
(2) Date: Apr. 8, 2016

(87) PCT Pub. No.: WO2015/053376
PCT Pub. Date: Apr. 16, 2015

(65) Prior Publication Data
US 2016/0244721 A1    Aug. 25, 2016

(30) Foreign Application Priority Data

Oct. 9, 2013 (JP) .............................. JP2013-212345

(51) Int. Cl.
*C12N 5/079* (2010.01)
*A61K 35/30* (2015.01)
*A61K 9/00* (2006.01)

(52) U.S. Cl.
CPC .......... *C12N 5/0621* (2013.01); *A61K 9/0048* (2013.01); *A61K 35/30* (2013.01); *C12N 2501/727* (2013.01); *C12N 2506/45* (2013.01); *C12N 2509/00* (2013.01); *C12N 2533/52* (2013.01)

(58) Field of Classification Search
None
See application file for complete search history.

(56) References Cited

U.S. PATENT DOCUMENTS

| 2008/0044901 A1 | 2/2008 | Sasai et al. |
| 2009/0142835 A1 | 6/2009 | Kobayashi et al. |
| 2011/0027333 A1 | 2/2011 | Idelson et al. |
| 2012/0220031 A1 | 8/2012 | Sekiguchi et al. |
| 2013/0196369 A1 | 8/2013 | Hikita et al. |
| 2014/0057281 A1 | 2/2014 | Takahashi et al. |
| 2016/0237403 A1 | 8/2016 | Sawada et al. |

FOREIGN PATENT DOCUMENTS

| EP | 3056563 A1 | 8/2016 |
| JP | 2012-080821 A | 4/2012 |
| JP | 2013-212345 A | 10/2013 |
| WO | WO 2005/123902 A1 | 12/2005 |
| WO | WO 2007/046501 A1 | 4/2007 |
| WO | WO 2008/129554 A1 | 10/2008 |
| WO | WO 2011/043405 A1 | 4/2011 |
| WO | WO 2012/115244 A1 | 8/2012 |
| WO | WO 2013/069503 A1 | 5/2013 |

OTHER PUBLICATIONS

Osakada et al., Journal of Cell Science, vol. 122, No. 17, 2009, pp. 3169-3179.*
Sonoda et al., Nat Protoc. 2009; 4(5): 662-673.*
Stemcell Technologies, Human Recombinant bFGF, retrieved from the internet Jan. 15, 2021: https://www.stemcell.com/human-recombinant-bfgf.html (Year: 2021).*
European Patent Office, Supplementary European Search Report in European Patent Application No. 14852053.9 (dated Jun. 28, 2017).
Kuroda et al., *PLoS One*, 7(5): e37342 (2012).
Higuchi et al., *Journal of Membrane Science*, 366: 286-294 (2011).
Miyazaki et al., *Nature Communications*, 3: 1236 (Dec. 4, 2012—updated Jul. 29, 2013).
Peng et al., "Tight Junctions of RPE Derived from Human Embryonic Stem Cells," *Visionary Genomics*, program/poster 2237/A403 (May 2, 2011).
Rodin et al., *Nature Biotechnology*, 28(6): 611-615 (2010).
Rowland et al., *Journal of Tissue Engineering and Regenerative Medicine*, 7: 642-653 (2013).
Sekiguchi et al., *Clinical Evaluation*, 41(1): 124-127 (2013).
Taniguchi et al., *The Journal of Biological Chemistry*, 284(12): 7820-7831 (2009).
Zhu et al., *PLoS One*, 8(1): e54552 (2013).
Japanese Patent Office, International Search Report in International Patent Application No. PCT/JP2014/077112 (dated Jan. 13, 2015).
The International Bureau of WIPO, International Preliminary Report on Patentability and Written Opinion of the International Searching Authority in International Patent Application No. PCT/JP2014/077112 (dated Apr. 12, 2016).
Miyazaki et al., "Laminin E8 fragments support efficient adhesion and expansion of dissociated human pluripotent stem cells," *Nat Commun.*, 3: 1236 including Erratum and Supplementary Information (Dec. 4, 2012—updated Jul. 29, 2013).

(Continued)

*Primary Examiner* — Evelyn Y Pyla
(74) *Attorney, Agent, or Firm* — Leydig, Voit & Mayer, Ltd.

(57) ABSTRACT

The present invention provides a method of purifying highly pure retinal pigment epithelial cells from a cell population obtained by induction of differentiation of pluripotent stem cells into retinal pigment epithelial cells, by a simple and easy operation in a short period. The purification method of the present invention includes a step of introducing a cell population containing retinal pigment epithelial cells obtained by differentiation induction of pluripotent stem cells on laminin or a fragment thereof on a filter, and obtaining a cell population that passed the filter.

10 Claims, 4 Drawing Sheets

Specification includes a Sequence Listing.

(56) References Cited

OTHER PUBLICATIONS

Aumailley, "A simplified laminin nomenclature," *Matrix Biol.*, 24(5): 326-332 (2005).

Aumailley, "The laminin family," *Cell Adh. Migr.*, 7(1): 48-55 (2013).

Durbeej et al., "Dystroglycan binding to laminin α1LG4 module influences epithelial morphogenesis of salivary gland and lung in vitro," *Differentiation*, 69(2-3): 121-134 (2001).

Galvin et al., "Dystroglycan modulates the ability of insulin-like growth factor-1 to promote oligodendrocyte differentiation," *J. Neurosci. Res.*, 88(15): 3295-3307 (2010).

Muschler et al., "Division of Labor among the α6β4 Integrin, β1 Integrins, and an E3 Laminin Receptor to Signal Morphogenesis and β-Casein Expression in Mammary Epithelial Cells," *Mol. Biol. Cell*, 10(9): 2817-2828 (1999).

Schéele et al., "Laminin α1 globular domains 4-5 induce fetal development but are not vital for embryonic basement membrane assembly," *Proc. Natl. Acad. Sci. U.S.A.*, 102(5): 1502-1506 (2005).

U.S. Appl. No. 15/028,076, filed Apr. 8, 2016.

Klimanskaya et al., "Derivation and Comparative Assessment of Retinal Pigment Epithelium from Human Embryonic Stem Cells Using Transcriptomics," *Cloning and Stem Cells*, 6(3): 217-245 (2004).

Rowland et al., Differentiation of Human Pluripotent Stem Cells to Retinal Pigmented Epithelium in Defined Conditions Using Purified Extracellular Matrix Proteins, *J. Tissue Eng. Regen. Med.*, 7(8): 642-653 (2013).

Sorkio et al, "Structure and Barrier Properties of Human Embryonic Stem Cell-Derived Retinal Pigment Epithelial Cells Are Affected by Extracellular Matrix Protein Coating," *Tissue Engineering: Part A*, 20(3-4): 622-634 (2014).

European Patent Office, Communication and Notice of Opposition in European Patent Application No. 14852053.9 (dated Apr. 25, 2022).

\* cited by examiner expression of RPE-related genes configuration of each lane

| lane | gene name | sample |
|---|---|---|
| 1 | marker | 100bp DNA ladder |
| 2 | BEST1 | 1120C7 |
| 3 | | 201B7 |
| 4 | | negative control (water) |
| 5 | | positive control (Lonza Human RPE) |
| 6 | Blank | water |
| 7 | RPE65 | 1120C7 |
| 8 | | 201B7 |
| 9 | | negative control (water) |
| 10 | | positive control (Lonza Human RPE) |
| 11 | Blank | water |
| 12 | Blank | water | state of cells after differentiation induction
and immediately before purification step
cells used 1120C7

METHOD FOR PURIFICATION OF RETINAL PIGMENT EPITHELIAL CELLS

CROSS-REFERENCE TO RELATED APPLICATIONS

This patent application is the U.S. national phase of International Patent Application No. PCT/JP2014/077112, filed Oct. 9, 2014, which claims the benefit of Japanese Patent Application No. 2013-212345, filed on Oct. 9, 2013, which are incorporated by reference in their entireties herein.

Incorporation-by-Reference of Material Electronically Submitted

Incorporated by reference in its entirety herein is a computer-readable nucleotide/amino acid sequence listing submitted concurrently herewith and identified as follows: 1,872 bytes ASCII (Text) file named "723742SequenceListing.txt," created Apr. 7, 2016.

TECHNICAL FIELD

The present invention relates to a method of purifying retinal pigment epithelial cells from a cell population obtained by induction of differentiation of pluripotent stem cells into retinal pigment epithelial (RPE) cells, a production method of retinal pigment epithelial cells, which uses said method, and the like.

BACKGROUND ART

As a method for producing retinal pigment epithelial cells from pluripotent stem cells, a method called SFEB method including culturing ES cells as a floating aggregate in a serum-free medium (patent document 1 etc.), a method including inducing differentiation of pluripotent stem cells in the presence of a differentiation-inducing factor on a culture substrate coated with a weakly cell adhesive coating agent and the like (non-patent document 1 etc.) are known. However, due to the low differentiation induction efficiency, these methods require plural steps combining adhesion culture and floating culture to obtain a highly concentrated cell population of retinal pigment epithelial cells, and have problems such as the required presence of a purification step with a high workload and a long time, which includes selectively picking up a colony of pigment cells under an optical microscope. These methods can obtain only a part of the RPE cells induced in a culture container, and the purity of the obtained cells is largely influenced by the technique of the experimenter, which problematically makes the methods unsuitable for large-scale production. Accordingly, a method capable of stably affording highly pure retinal pigment epithelial cells by a simple and easy method even when RPE cells are produced at a large scale has been demanded.

For maintenance culture of human pluripotent stem cells, a method using an extracellular matrix instead of a feeder cell has been widely used. Among others, laminin is being preferably used and, for example, non-patent document 2 reports successful maintenance culture of human ES cell on laminin-511 for a long term. As for E8 fragment known as an altered laminin having an improved cell adhesion activity, for example, patent document 2 and non-patent document 3 disclose culture methods of human pluripotent stem cells, which use E8 fragment of human laminin-α5β1γ1 (laminin-511E8, hereinafter indicated in the same manner) and human laminin-322E8. Non-patent document 4 describes that laminin-511E8 maintains binding activity to α6β1 integrin, which is of the same level as that of full-length laminin-511, and patent document 2 describes that, by using said laminin-511E8, pluripotent stem cells can be stably immobilized on a culture dish, as a result of which the cells, while maintaining differentiation pluripotency, can be subjected to maintenance culture. However, no report has documented utilization of such E8 fragment of laminin for other than culture of pluripotent stem cells, for example, differentiation induction of pluripotent stem cells and the like.

On the other hand, as a method of inducing differentiation of human pluripotent stem cells into retinal pigment epithelial cells in the absence of a feeder cell, a method using laminin is known. For example, non-patent document 5 describes that the differentiation induction efficiency into retinal pigment epithelial cells markedly increased by adhesion culture of pluripotent stem cells on laminin-111 and MATRIGEL™ basement membrane preparation, which mainly comprises laminin. However, no report has documented use of the E8 fragment of laminin for the induction of differentiation of pluripotent stem cell into retinal pigment epithelial cell.

DOCUMENT LIST

Patent Documents patent document 1: WO 2005/123902
patent document 2: WO 2011/043405

Non-Patent Document non-patent document 1: PLoS One. 2012; 7(5): e37342.
non-patent document 2: Nature Biotech. June 2010; 28(6): 611-5
non-patent document 3: Nat. Commun. 3:1236 doi: 10.1038/ncomms2231
non-patent document 4: J Biol Chem. 284:7820-7831, 2009
non-patent document 5: J. Tissue Eng Regen Med 2013; 7: 642-653

SUMMARY OF THE INVENTION

Problems to be Solved by the Invention

An object of the present invention is to provide a method of purifying highly pure retinal pigment epithelial cells from a cell population obtained by induction of differentiation of pluripotent stem cells into retinal pigment epithelial cells, by a simple and easy operation in a short period.

Means of Solving the Problems

The present inventors have conducted intensive studies in an attempt to achieve the above-mentioned objects and found that, when human pluripotent stem cells are cultured on a culture substrate coated with laminin-E8, the seeded pluripotent stem cells rapidly adhere to the culture substrate, a large amount of pigment cell is generated from early stages, the yield of retinal pigment epithelial cells can be markedly improved, and not only retinal pigment epithelial cells but also other visual cell-lineage cells are produced together with matrix components. The present inventors have further found that retinal pigment epithelial cells alone can be efficiently purified from retinal pigment epithelial cells produced on laminin even though they lie buried in other cells and matrix components, by a simple operation of introducing all of these on a filter. They have further found that the low recovery rate, which is the problems in inducing differentiation of pluripotent stem cells into retinal pigment epithelial cells can be markedly improved, and the desired retinal pigment epithelial cells can be conveniently and stably purified. The present inventor have thereafter conducted intensive studies and completed the present invention.

That is, the present invention relates to the following.

[1] A method of purifying a retinal pigment epithelial cell, comprising a step of introducing a cell population containing retinal pigment epithelial cells obtained by differentiation induction of pluripotent stem cells on laminin or a fragment thereof on a filter, and obtaining a cell population that passed the filter.
[2] The method of the above-mentioned [1], wherein the laminin or a fragment thereof is a laminin-E8 fragment.
[3] The method of the above-mentioned [1] or [2], wherein the cell population containing the retinal pigment epithelial cells is recovered by treating with a cell separating solution after the differentiation induction.
[4] The method of the above-mentioned [3], wherein the cell separating solution comprises trypsin.
[5] The method of any of the above-mentioned [1]-[4], wherein the filter has a pore size of 20-70 μm.
[6] A method of producing a retinal pigment epithelial cell from a pluripotent stem cell, comprising
(1) a step of obtaining a cell population containing retinal pigment epithelial cells by inducing differentiation of a pluripotent stem cell on laminin or a fragment thereof; and
(2) a step of introducing the cell population obtained in (1) on a filter to obtain a cell population that passed the filter.
[7] The method of the above-mentioned [6], wherein the laminin or a fragment thereof is a laminin-E8 fragment.
[8] The method of the above-mentioned [6] or [7], wherein the cell population obtained in step (1) is recovered by treating the cell population containing the retinal pigment epithelial cells with a cell separating solution.
[9] The method of the above-mentioned [8], wherein the cell separating solution comprises trypsin.
[10] The method of any of the above-mentioned [6]-[9], wherein the filter has a pore size of 20-70 μm.
[11] A retinal pigment epithelial cell obtained by the method of any of the above-mentioned [6]-[10].
[12] A retinal pigment epithelial cell sheet obtained by the method of any of the above-mentioned [6]-[10].

Effect of the Invention

According to the present invention, retinal pigment epithelial cells induced from pluripotent stem cells can be conveniently purified in a high yield.

DESCRIPTION OF EMBODIMENTS

Figure 1:
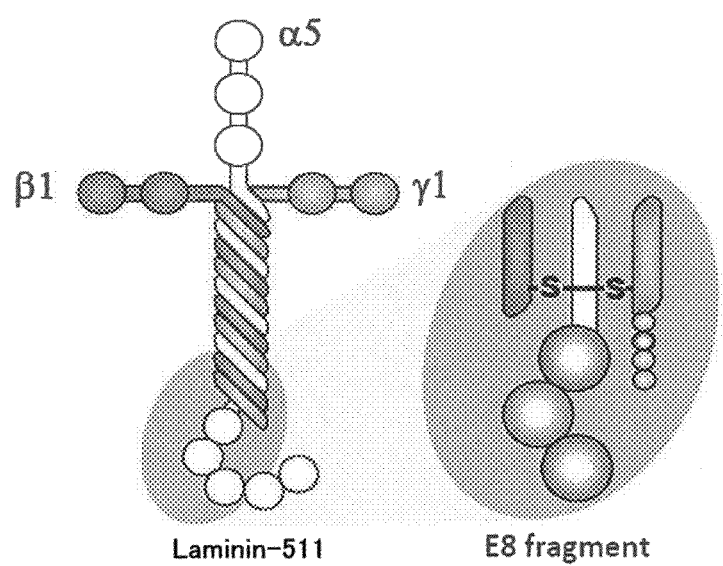
FIG. 1 is a schematic showing of the structure of laminin-E8.

1. Purification Method and Production Method of Retinal Pigment Epithelial Cell

The present invention relates to a method of purifying a retinal pigment epithelial cell, comprising introducing a cell population containing retinal pigment epithelial cells obtained by differentiation induction of pluripotent stem cells on laminin or a fragment thereof on a filter (hereinafter to be also referred to as the purification method of the present invention). The present invention also relates to a method of producing a retinal pigment epithelial cell from a pluripotent stem cell, which is characterized by the use of said method (hereinafter to be also referred to as the production method of the present invention). The production method of the present invention contains the following two largely-divided steps:
(1) a step of obtaining a "cell population containing retinal pigment epithelial cells" by inducing differentiation of a pluripotent stem cell on laminin or a fragment thereof; and
(2) a step of introducing "the cell population containing the retinal pigment epithelial cells" obtained in (1) on a filter to purify the retinal pigment epithelial cells. The purification method of the present invention targets the above-mentioned step (2). Each step is explained in detail below.
(1) Step of Obtaining Cell Population Containing Retinal Pigment Epithelial Cells In step (1), pluripotent stem cells are subjected to differentiation induction by adhesion culture using a culture substrate coated with laminin or a fragment thereof, and a cell population containing the retinal pigment epithelial cells is obtained.

The "pluripotent stem cell" in the present invention means a stem cell having self-replication competence and differentiation pluripotency, and is not particularly limited. For example, embryonic stem cells (ES cell), induced pluripotent stem cells (iPS cell) and the like are widely utilized. Preferably, human ES cells or human iPS cells are utilized and, more preferably, human iPS cells are utilized.

The "iPS cell" in the present invention means a cell that artificially acquired self-replication competence and differentiation pluripotency by contacting a nuclear reprogramming factor with somatic cells (e.g., fibroblast, skin cell, lymphocyte etc.). The production method of iPS cells in the present invention is not particularly limited.

In the present invention, as the pluripotent stem cell, a pluripotent stem cell derived from a mammal can be used. While the mammal is not particularly limited, it is preferably human from the aspect of clinical application.

The "retinal pigment epithelial cell" in the present invention refers to an epithelial cell constituting the retinal pigment epithelium, and a progenitor cell thereof. Whether a retinal pigment epithelial cell or not can be confirmed by, for example, expression of cell markers (RPE65, CRALBP, MERTK, BEST1 etc.), cell forms (intracellular melanin dye deposition, polygonal and flat cell form, formation of polygonal actin bundle etc.) and the like. The progenitor cell of retinal pigment epithelial cell means a cell directed to be induced to differentiate into retinal cell, and whether a progenitor cell or not can be confirmed by expression of cell markers (Mitf (pigment epithelial cell, progenitor cell), Pax6 (progenitor cell), Rx (retinal progenitor cell), Crx (photoreceptor precursor cell), Chx10 (bipolar cell) etc.) and the like. Functional evaluation of retinal pigment epithelial cell can be confirmed using, for example, secretability, phagocytic capacity and the like of cytokine (VEGF, PEDF etc.) as an index. These functional evaluation and confirmation operations can be performed by those of ordinary skill in the art by setting appropriate conditions.

The "laminin" in the present invention is a heterotrimer molecule consisting of α, β, γ chains, and is an extracellular matrix protein containing isoforms having different subunit chain compositions. Specifically, laminin has about 15 kinds of isoforms including heterotrimers of combinations of 5 kinds of α chain, 4 kinds of β chain and 3 kinds of γ chain. The number of each of α chain (α1-α5), β chain (β1-β4) and γ chain (γ1-γ3) is combined to determine the name of laminin. For example, a laminin composed of a combination of α1 chain, β1 chain, γ1 chain is named laminin-111, a laminin composed of a combination of α5 chain, β1 chain, γ1 chain is named laminin-511, and a laminin composed of a combination of α5 chain, β2 chain, γ1 chain is named laminin-521. As laminin, for example, a laminin derived from a mammal can be used. Examples of the mammal include mouse, rat, guinea pig, hamster, rabbit, cat, dog, sheep, swine, bovine, horse, goat, monkey and human. Human laminin is preferably used when retinal pigment epithelial cells are produced for the purpose of transplanting to human, and the like. At the present stage, human laminin is known to include 15 kinds of isoforms.

As laminin in the present invention, any isoform can be used. For example, laminin isoform showing binding specificity to at least one of the integrins expressed on the surface of human pluripotent stem cell and/or human retinal pigment epithelial cell, preferably laminin isoform showing binding specificity to integrin expressed on the surface of human pluripotent stem cell and human retinal pigment epithelial cell, and integrin expressed on the surface of human retinal pigment epithelial cell, is preferably used. Examples of the integrin expressed on the surface of human pluripotent stem cell include α6β1 integrin and the like, and examples of the integrin expressed on the surface of human retinal pigment epithelial cell include α6β1 integrin, α3β1 integrin, α7β1 integrin and the like. From the above, as a preferable laminin, one showing binding specificity to α6β1 integrin, and capable of stably adhering pluripotent stem cells in the initial stage of differentiation induction and retinal pigment epithelial cells in the latter stage of differentiation induction or a progenitor cell thereof is preferably used. From such aspect, laminin 511 and laminin 521 are preferable in laminin isoforms. Laminin 511 has binding specificity to α6β1 integrin as well as α3β1 integrin and α7β1 integrin, and laminin 521 has binding specificity to α6β1 integrin as well as stronger binding specificity to α3β1 integrin. Therefore, these isoforms contribute to the improvement of differentiation induction efficiency of pluripotent stem cells into retinal pigment epithelial cells, or stabilization of maintenance culture of retinal pigment epithelial cells, by improving adhesion activity to retinal pigment epithelial cells.

The laminin fragment in the present invention may be any as long as it retains the function of each corresponding laminin. That is, the "laminin fragment" in the present invention is not limited as to the length of each chain as long as it is a molecule having laminin α chain, β chain and γ chain constituting a heterotrimer, retaining binding activity to integrin, and maintaining cell adhesion activity. The laminin fragment shows integrin binding specificity that varies for the original laminin isoform, and can exert an adhesion activity to a cell that expresses the corresponding integrin. As such laminin fragment, preferred is a laminin-E8 fragment.

Laminin-E8 fragment was originally one of the fragments obtained by digesting mouse laminin-111 with elastase, and identified as a fragment having strong cell adhesion activity (EMBO J., 3:1463-1468, 1984., J. Cell Biol., 105:589-598, 1987.). When digested with elastase, the presence of a fragment corresponding to the E8 fragment of mouse laminin-111 is assumed in laminin other than mouse laminin-111. However, separation and identification of E8 fragment by digestion of laminin other than mouse laminin-111 with elastase has not been reported heretofore. Therefore, laminin-E8 fragment to be used in the present invention is not required to be an elastase digestion product of each laminin, but may be a recombinant as long as it is a fragment of laminin having a cell adhesion activity similar to that of each corresponding laminin and having a structure corresponding to that of E8 fragment digested with elastase. That is, the "laminin-E8 fragment (hereinafter sometimes to be indicated as "laminin-E8")" in the present invention refers to a molecule constituting a heterotrimer in each C-terminal region of α chain, β chain and γ chain, maintaining a binding activity to integrin, as well as maintaining a cell adhesion activity. Laminin-E8 shows integrin binding specificity that varies for each laminin isoform, and can exert a strong adhesion activity to a cell that expresses the corresponding integrin.

When concretely explained, laminin-E8 in the present invention is a laminin fragment having,
(1) functionally, cell adhesion activity at least equivalent to that of full-length laminin, and at least equivalent integrin binding activity, and
(2) structurally, a structure corresponding to that of mouse laminin-E8, specifically, a structure corresponding to a region from coiled-coil C-terminal region of laminin trimer to 1st-3rd of G domain. The laminin fragment, particularly laminin-E8, is explained in more detail in the following from the (1) functional aspect and (2) structural aspect.
(1) Function of Laminin Fragment Examples of the laminin fragment in the present invention include a molecule showing binding specificity to at least one of the integrins expressed on the surface of human pluripotent stem cell and/or human retinal pigment epithelial cell, preferably, a molecule showing binding specificity to an integrin expressed on the surface of both human pluripotent stem cells and human retinal pigment epithelial cells, and an integrin expressed on the surface of human retinal pigment epithelial cells are preferably used. These integrins are as described above.

Laminin fragment in the present invention shows binding specificity to integrin, preferably shows at least equivalent binding specificity to each corresponding laminin. Laminin fragment showing particularly strong affinity to integrin is preferably used. "Laminin fragment showing particularly strong affinity to integrin" is one showing a significantly low dissociation constant as measured by a known method and, for example, the dissociation constant measured by, for example, the method shown in Table 1 of The Journal of Biological Chemistry (2009) 284, pp. 7820-7831 is not more than 10 nM.

As the laminin fragment in the present invention, one having cell adhesion activity, preferably strong cell adhesion activity, is used. The "laminin fragment having a strong cell adhesion activity" is one showing a significantly strong adhesion activity in a cell adhesion test with measurement by a known method and shows an adherent cell number of not less than 400 cells/mm² at a coating concentration of said fragment of not more than 10 nM when, for example, the cell adhesion assay described in The Journal of Biological Chemistry (2007) 282, pp. 11144-11154 is performed.

In the present invention, as laminin fragment, one showing binding specificity to α6β1 integrin, capable of stably adhering pluripotent stem cells in the initial stage of differentiation induction, and capable of stably adhering retinal pigment epithelial cells in the latter stage of differentiation induction or progenitor cells thereof is preferably used. From such aspect, a fragment of laminin-511 or laminin-521 or the like is preferable among the laminin fragments, and particularly preferred are laminin-511 E8 and laminin-521 E8. Laminin-511 E8 has binding specificity to α3β1 integrin and α7β1 integrin in addition to α6β1 integrin, and laminin-521 E8 has binding specificity to α6β1 integrin as well as stronger binding specificity to α3β1 integrin in addition to α6β1 integrin. Therefore, such laminin-E8 can contribute to the improvement of differentiation induction efficiency of pluripotent stem cells into retinal pigment epithelial cells, by improving the adhesion activity to retinal pigment epithelial cells. Alternatively, such laminin-E8 can contribute to the stabilization of maintenance culture of retinal pigment epithelial cells.

(2) Structure of Laminin Fragment

The laminin fragment in the present invention is not limited as to the length of each chain as long as it is a molecule having laminin α chain, β chain and γ chain constituting a heterotrimer, retaining binding activity to integrin, and maintaining cell adhesion activity. Such laminin fragment can be appropriately designed by those of ordinary skill in the art who understand the structure of each domain of laminin and the like. Of such laminin fragments, as mentioned above, it is preferably, as mentioned above or shown in FIG. 1, a laminin fragment structurally corresponding to a fragment having a cell adhesion activity (E8 fragment) in an elastase digestion product of mouse laminin-111. That is, it maintains a part of domain II (triple-stranded coiled-coil domain) of full-length laminin (E8 fragment depicted in FIG. 1 does not show such manner but actually maintains a coiled-coil structure), and forms a short coiled-coil structure on the N terminal side of E8 with a corresponding fragment of β chain and a corresponding fragment of γ chain. On the C-terminal side of E8, the G1-G3 domain structure of α chain is maintained. The β chain and γ chain are bonded to each other by forming a disulfide bond via a cysteine residue on each C-terminal side.

As described above as regards laminin-E8, laminin fragment in the present invention may be an enzyme-treated product obtained by treating natural laminin with elastase, or a recombinant produced by gene recombination.

When the laminin or a fragment thereof in the present invention is a recombinant, a tag may be bonded to the N terminal for the purpose of purification and the like as long as the binding activity of the corresponding full-length (natural) laminin to integrin is maintained, and the cell adhesiveness is not impaired. Such tag is not particularly limited and, for example, His tag, Flag tag, HA tag and the like can be mentioned. Also, the sequence of the linker region between the tag and laminin or a fragment thereof is not particularly limited as long as the binding activity of the corresponding full-length (natural) laminin to integrin is maintained, and cell adhesiveness is not impaired.

In the laminin or a fragment thereof in the present invention, a part of the amino acid sequence may be deleted, added, or substituted as long as the binding activity of the corresponding laminin to integrin is maintained, and the cell adhesiveness thereof is not impaired.

While E8 fragment generally lacks two G domains (G4 and G5) on the α chain C-terminal side, the G4, G5 domains may be partly or entirely contained in the laminin-E8 in the present invention as long as the binding activity of the corresponding full-length (natural) laminin to integrin is maintained, and cell adhesiveness thereof is not impaired. For example, the G4, G5 domains may be partly or entirely contained in the laminin-511 E8 as long as the binding activity to integrin α6β1 of the equivalent level as laminin-511 is maintained, and the cell adhesion activity is not impaired.

Like full-length laminin, β chain and γ chain of laminin-E8 are bonded via cysteine on the C-terminal side of the coiled-coil part. Since the cysteine influences the integrin binding activity, it is desirably not substituted or deleted. Furthermore, since the C-terminal side amino acid following said cysteine in the γ chain also influences the integrin binding activity, it is desirably at least not deleted (J Biol Chem. 2007 Apr. 13; 282(15):11144-54.).

Specific examples of such laminin-E8 include rhLM511E8 produced in Example (3) of WO 2011/043405. Said laminin-511E8 can be preferably utilized as the laminin-E8 in the present invention.

The "culture substrate" to be used in the present invention can be produced by coating a surface of an incubator with the laminin or a fragment thereof in the present invention. As used herein, "coating" a surface of an incubator means adsorption of laminin or a fragment thereof to the surface of the incubator by some interaction between laminin or a fragment thereof and the incubator surface, where the orientation of the laminin or a fragment thereof does not pose a particular problem in affording the effect of the present invention. The incubator is not particularly limited as long as it can be used for cell culture and, for example, dish (also referred to as culture dish), petri dish and plate (microtiter plate, microplate, deep well plate etc. of 6 well, 24 well, 48 well, 96 well, 384 well, 9600 well and the like), flask, chamber slide, tube, Cell Factory, roller bottle, spinner flask, hollow fiber, microcarrier, bead and the like can be mentioned. The culture substrate in the present invention may be applied with an appropriate surface treatment as long as the cell adhesion property by laminin or a fragment thereof is not impaired.

The "adhesion culture" in the present invention means culture in a state where the cells of interest are adhered to the bottom of the incubator via laminin or a fragment thereof, and do not float in the culture medium even when the incubator is gently shaken during culture. Since laminin or a fragment thereof to be used in the present invention can show extremely superior cell adhesiveness, the cells after cell seeding are preferably uniformly dispersed by a method including rapidly trembling the incubator and the like. The cells of interest may be subjected to floating culture in an incubator containing laminin or a fragment thereof before and after the adhesion culture, as long as the object of the present invention can be achieved.

The medium is constituted of a basal medium, a serum and/or a serum replacement, and other components. As the basal medium, one or plural kinds of synthetic media generally used for culturing mammalian cells can be used in combination and, for example, commercially available products such as DMEM, GMEM and the like can be obtained.

As the serum, a serum derived from a mammal such as bovine, human, swine and the like can be used. The serum replacement is a low-protein replacement that replaces serum such as FBS and the like used for the cell culture, and commercially available products such as Knockout Serum Replacement (KSR), Chemically-defined Lipid concentrated (manufactured by Gibco), Glutamax (manufactured by Gibco) and the like, as well as N2, B27 and the like which are serum replacements for nerve cell culture can be obtained. Preferably, an appropriate amount of albumin and cytokine purified or produced by recombination, further a lipid mixture and the like can also be independently combined with the basal medium. In the present invention, a serum replacement is preferable, and KSR is particularly preferable from the aspect of quality management of the cell of interest.

The concentration of serum or serum replacement can be appropriately set within the range of, for example, 0.5-30% (v/v). The concentration may be constant, or gradually changed. For example, the concentration may be lowered in stages at intervals of about 1-3 days (preferably 2 days). For example, serum or serum replacement can be added at 3 stages of concentration of 20%, 15% and 10%.

As other component constituting the medium, a Rho kinase inhibitor such as Y-27632 and the like can be used to suppress cell death of human pluripotent stem cells dispersed in a culture medium. A Rho kinase inhibitor may be added in the period of a part or the whole period of the differentiation induction step. For example, unnecessary cells that did not differentiate into the cell of interest can be removed by cell death by using a medium free of a Rho kinase inhibitor in the latter period of the differentiation induction step.

The medium can contain other components generally used for culturing mammalian cells, besides those mentioned above.

The concentration of human pluripotent stem cells to be used in the production method of the present invention is not-particularly limited as long as pluripotent stem cells can be uniformly seeded, and adhesion culture is possible. For example, when a 10 cm dish is used, it is $1 \times 10^5$-$1 \times 10^8$ cells, preferably $2 \times 10^6$-$5 \times 10^7$ cells, more preferably $5 \times 10^5$-$9 \times 10^6$ cells, per 1 dish.

The adhesion culture in the production method of the present invention can also be performed in the presence of a differentiation-inducing factor. As the differentiation-inducing factor, a factor known as a factor promoting differentiation induction into the cell of interest can be utilized. Since the production method of the present invention includes differentiation induction into retinal pigment epithelial cells, a differentiation-inducing factor into retinal pigment epithelial cells is desirably used. Examples of the differentiation-inducing factor into retinal pigment epithelial cells include Nodal signal inhibitor, Wnt signal inhibitor, Sonic hedgehog signal inhibitor, and Activin signal promoter and the like.

The Nodal signal inhibitor is not particularly limited as long as it can suppress signal transduction mediated by Nodal, and protein, nucleic acid, low-molecular-weight compound and the like can be used. Examples of the Nodal signal inhibitor include protein, peptide or nucleic acid such as Lefty-A, soluble Nodal receptor, anti-Nodal antibody, Nodal receptor inhibitor and the like; low-molecular-weight compound such as SB-431542 and the like, and the like. Particularly, a low-molecular-weight compound such as SB-431542 and the like which is easily available and shows less difference between lots is preferable.

The Wnt signal inhibitor is not particularly limited as long as it can suppress signal transduction mediated by Wnt, and protein, nucleic acid, low-molecular-weight compound and the like can be used. Examples of the Wnt signal inhibitor include protein, peptide or nucleic acid such as Dkkl, Cerberus protein, Wnt receptor inhibitor, soluble Wnt receptor, Wnt antibody, casein kinase inhibitor, dominant negative Wnt protein and the like; and low-molecular-weight compound such as CKI-7(N-(2-aminoethyl)-5-chloro-isoquinoline-8-sulfonamide), D4476(4-{4-(2,3-dihydrobenzo[1,4]dioxin-6-yl)-5-pyridin-2-yl-1H-imidazol-2-yl}benzamide), IWR-1-endo(IWR1e), IWP-2 and the like. Particularly, a low-molecular-weight compound which is easily available and shows less difference between lots is preferable. Among others, a low-molecular-weight compound having an activity to selectively inhibit casein kinase I is preferable and, for example, CKI-7, D4476 and the like can be utilized.

Examples of the Activin signal promoter include protein belonging to the Activin family, Activin receptor, Activin receptor agonist and the like.

The concentration of these differentiation-inducing factors can be appropriately selected according to the kind of the differentiation-inducing factor. Specifically, when SB-431542 is used as a Nodal signal inhibitor, the concentration is, for example, 0.01-50 μM, preferably 0.1-10 μM, more preferably 5 μM; when CKI-7 is used as a Wnt signal inhibitor, it is added at the concentration of 0.01-30 μM, preferably 0.1-30 μM, more preferably 3 μM.

In the production method of the present invention, a combination of a Nodal signal inhibitor (e.g., SB-431542) and a Wnt signal inhibitor (e.g., CKI-7) is preferably used as a differentiation-inducing factor.

Culture according to the aforementioned method induces differentiation of pluripotent stem cells into retinal pigment epithelial cells, whereby retinal pigment epithelial cells can be generated generally on day 25-45 from the seeding of pluripotent stem cells. Generation of retinal pigment epithelial cell can be confirmed according to the aforementioned method. When generation of retinal pigment epithelial cells is confirmed, the medium is exchanged with a maintenance medium for retinal pigment epithelial cells and, for example, the cells are preferably further cultured for 5-10 days while exchanging the total amount of medium at a frequency of not less than once in 3 days. As a result, a melanin dye deposition cell population and a polygonal flat cell population adhered to the basal lamina can be observed more clearly.

As the maintenance medium for retinal pigment epithelial cells, for example, those described in IOVS, March 2004, Vol. 45, No. 3, Masatoshi Haruta, et. al., IOVS, November 2011, Vol. 52, No. 12, Okamoto and Takahashi, J. Cell Science 122 (17), Fumitaka Osakada, et. al., IOVS, February 2008, Vol. 49, No. 2, Gamm, et. al. can be used, which are constituted of a basal medium, a serum and/or a serum replacement, and other components. As the basal medium, one or plural kinds of synthetic media generally used for culturing mammalian cells can be used in combination and, for example, commercially available products such as DMEM, GMEM and the like can be obtained.

As the serum, a serum derived from a mammal such as bovine, human, swine and the like can be used. The serum replacement is a low-protein replacement that replaces serum such as FBS and the like used for the cell culture, and commercially available products such as Knockout Serum Replacement (KSR), Chemically-defined Lipid concentrated (manufactured by Gibco), Glutamax (manufactured by Gibco) and the like, as well as N2, B27 and the like which are serum replacements for nerve cell culture can be obtained. In the present invention, a serum replacement is preferable, and B27 is particularly preferable from the aspect of quality management of the cell of interest.

Examples of other components include L-glutamine, penicillin sodium, sulfuric acid streptomycin and the like.

The cell population containing the retinal pigment epithelial cells obtained by culture according to the present invention, can include, in addition to retinal pigment epithelial cell, cells such as visual cell-like cell, nerve-like cell, neuroglia cell, Muller cell, amacrine cell, bipolar cell, horizontal cell, ganglion cell, as well as various matrix components such as polysaccharides, phospholipid, and adhesion protein and the like. More specifically, in the culture according to the present invention, after seeding pluripotent stem cells, the cells are rapidly adhered to and fixed on the incubator via laminin-E8 superior in cell adhesion, and cells are abundantly layered covering the cells adhered to the incubator to form a cell layer exhibiting various forms, namely, a composite cell layer structure wherein a cell layer having a mild elevation and covering the whole is the base, and a tubular and funicular structure or cobweb-like or circular cell group is formed thereon, is formed by around day 20 from the seeding of the pluripotent stem cells. After formation of the structure, by further continuing the culture, the retinal pigment epithelial cells can be induced and produced while being buried in a viscose substance (jelly-like substance) that apparently seems to be a mixture of visual cells and extracellular matrix components such as various matrix proteins, polysaccharides, and phospholipids.

(2) Step of Purifying Retinal Pigment Epithelial Cells by Introducing "Cell Population Containing the Retinal Pigment Epithelial Cells" Obtained in (1) on Filter In this step, to purify retinal pigment epithelial cells from the "cell population containing the retinal pigment epithelial cells" obtained in (1), the cell population is introduced on a filter as mentioned below.

The cell population containing retinal pigment epithelial cells is desirably obtained by differentiation induction of pluripotent stem cells as mentioned above, and may contain, besides retinal pigment epithelial cells of interest, retina precursor cells at various differentiation induction stages, visual cells and nerve cells not desired, and extracellular matrix components assumed to have been produced by these cells.

For example, in the SFEB method described in WO 2005/123902, it is necessary to culture stem cells in a special serum-free medium in the absence of a supporting cell under floating conditions to form aggregates, perform differentiation induction of immature nerve progenitor cells, and recover retina epithelial cell group under an optical microscope from non-adherent cell aggregates formed from such cells. Even in a method using a weakly cell adhesive coating agent such as poly-L-lysine and gelatin (modified SFEB method (described in US 20130224156 A1)), being similar to this method, a cell population containing retinal pigment epithelial cells after differentiation induction is dissociated to some degree, cell aggregates are once formed by floating culture, cell aggregates having a strong melanin producibility is selected under a microscope according to the level of color development or black-brown distribution, the cell aggregates are further subjected to adhesion culture, and cultured until they reach sufficient purity and cell number while manually removing irregularly-shaped or xenogeneic cells under a microscope when they grew, and then recovered. In such conventional methods not using laminin or a fragment thereof as a substrate, the emergence rate of retinal pigment epithelial cells was extremely low. Even when they are subjected to floating culture and grown to form cell aggregates, it was necessary to select cells other than the object cells for manual removal from each cell aggregate, since the object retinal pigment epithelial cells are integrated with the cells other than the object cells to form a tissue.

Therefore, when retinal pigment epithelial cells are induced to differentiate from pluripotent stem cells, not only retinal pigment epithelial cells of interest but also cells other than the object cells are generally obtained simultaneously by conventionally known methods. In addition, a complicated and specialized step to directly take out manually and purify retinal pigment epithelial cells since populations of retinal pigment epithelial cells (cell aggregate showing melanin black-brown) are visually confirmable but small in amount, and integrated with cell aggregates to form a tissue.

Figure 3:
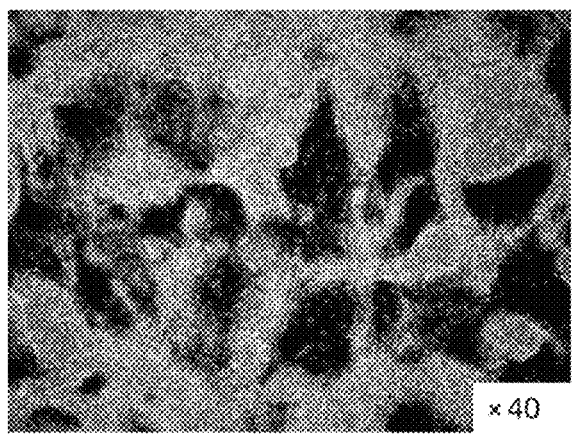
FIG. 3 shows the state of cultured cells immediately before purification.
Figure 3:
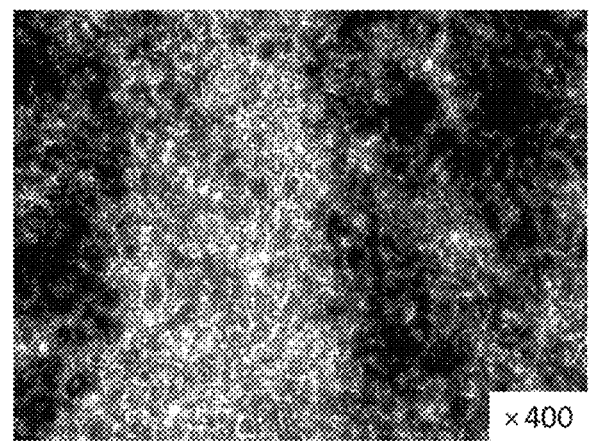

In the purification method or production method of the present invention, since laminin or a fragment thereof is employed as a substrate for differentiation induction, adhesion of iPS cells to the substrate is markedly dense. However, in the final stage of the differentiation induction step, not only retinal pigment epithelial cells but cells other than the object cells are abundantly obtained. By observation under an optical microscope, the cell population containing the retinal pigment epithelial cells was obtained simultaneously with a mixture (the above-mentioned jelly-like substance) of visual cells other than the object cells cell and extracellular matrix components assumed to have been produced by these cells, and apparently buried in a mixture of these (FIG. 3). Therefore, as in the above-mentioned modified SFEB method, they also need to be directly harvested under a microscope, and highly pure retinal pigment epithelial cells cannot be obtained conveniently and efficiently, where purification of retinal pigment epithelial cells by simply introducing them on a filter is not imaginable.

However, by close observation by the present inventors, it was found that differentiation-induced retinal pigment epithelial cells were not simply buried in the multi-layered cell mixture but present under a jelly-like substance containing other visual cells and the like (i.e., on laminin or a fragment thereof), due to strong adhesion to laminin or a fragment thereof as a substrate, without forming a mixture with the jelly-like substance. From such manner of presence of the cell population, an idea of a purification method of retinal pigment cells by introduction thereof on a filter was obtained. This purification method does not require a complicated, specialized and technical purification step unlike conventional methods, and is convenient, efficient, and extremely useful since it can be used for general purposes.

For introduction on a filter, the obtained cell population is detached from an incubator. Detachment may be performed by physically scraping off the cells from the contact surface with a pipetting or cell scraper etc. or by a treatment with a protease such as trypsin, collagenase, dispase and the like. Preferably, detachment is performed by a treatment with a protease such as trypsin, collagenase, dispase and the like. These treatments can be performed according to a method known per se.

The cell population after the above-mentioned detachment is preferably subjected to a treatment to dissociate adhesion between cells to some degree before introduction on a filter, so that the covering jelly-like substance will not fill the filter pores. The treatment can be performed, for example, by several times of reciprocating pipetting of the cell population. Excessive cell dissociation treatment is not desirable since it destroys the jelly-like substance. Furthermore, it is desirable to remove the protease solution and the residual impurities thereof, and matrix components and the like in the cell mixture together with the supernatant by centrifugation.

The cell population obtained as mentioned above is recovered, introduced on a filter. According to the method of the present invention, retinal pigment epithelial cells pass the filter, a mixture containing other cells (e.g., visual cell etc.) and various matrix components can be captured on the filter, and retinal pigment epithelial cells can be purified. The filter treatment in the present invention is not particularly limited as to the form and steps of filter and the like as long as it can realize the object. The filter treatment is explained in detail below.

As the material of the filter, those generally used for filtering cell culture media can be used. For example, it is a synthetic polymer selected from at least one kind of polyester, polypropylene, polystyrene, acryl, rayon, polyolefin, vinylon, polyethylene, nylon, polyurethane and the like. Preferred are nylon and the like showing low polarity and less adsorption of protein. Those showing high polarity and high ionic electric charge, or strong hydrophobicity are difficult to use since the surface of filter is easily covered with the jelly-like substance.

While the form of the filter may be a porous form with a communicating pore structure, an assembly of fibers, a fabric and the like, a non-woven fabric is more preferable. Use of a twisted fiber is not desirable since the jelly-like substance covers the filter surface to cause clogging.

The fiber diameter of the filter is not particularly limited as long as unnecessary components can be trapped and retinal pigment epithelial cells can pass through efficiently. In consideration of the passage of the retinal pigment epithelial cells, it is smaller than the pore size of the filter and, for example, 5-20 µm.

While the pore size of the filter is not particularly limited as long as unnecessary components can be trapped and retinal pigment epithelial cells can pass through efficiently, it is generally 15-100 µm. In consideration of the cell size and the trapping effect of unnecessary components, 20-70 µm is preferable, 20-40 µm is more preferable. When the pore size is less than 20 µm, the passage rate of retinal pigment epithelial cells may decrease and when it is larger than 100 µm, the trapping effect of unnecessary components may lead to a decrease in the trapping efficiency.

The pore size of filter can be measured by photographing a filter by a scanning electron microscope, measuring bores (maximum length) of a substantial pore formed by intersection of two or more different fibers by an image analyzer at 50 random points and determining the mean.

The use form of the filter may be any such as a sphere, container, cassette, bag, tube, column and the like. Specific preferable examples include a transparent or semitransparent cylindrical container having a volume of about 0.1-1000 ml and a diameter of about 0.1-15 cm, or a quadrangular prism form having a square or rectangle having the length of one side of about 0.1 cm-20 cm and a thickness of about 0.1 cm-5 cm and the like.

Passage of solution through the filter may be performed by natural dropping from a bag and the like containing a cell population (cell suspension), or by using a syringe or pump.

By the above operation, unnecessary components in the cell culture medium introduced on a filter are trapped by the filter and retinal pigment epithelial cells selectively pass the filter, whereby the cells can be purified. As for the number of cells in a liquid that passed the filter, for example, purity of retinal pigment epithelial cells of not less than 80%, preferably not less than 90%, more preferably not less than 95%, can be achieved. As for the purity, Pax6, Bestrophin or Mitf immunostaining is performed, when the cells are stained with any of them, the cells are determined to be retinal pigment epithelial cells, when fluorescence is not seen in the cells, the presence or absence of dark brown-black color development of melanin pigment in, the cell is examined and when generation of the pigment is confirmed, the cells can be determined to be retinal pigment epithelial cells. Furthermore, by seeding the obtained cell population in a new culture container coated with laminin or a fragment thereof and performing the purification operation again, the purity can be further improved. The yield of the retinal epithelial pigment cells obtained at this stage was about 50- to 100-fold than by the SFEB modification method.

According to the production method of the present invention, human pluripotent stem cells can be rapidly adhered to an incubator via laminin or a fragment thereof superior in cell adhesion, and culture in an immobilized state markedly improves differentiation induction efficiency and, moreover, cell loss during medium exchange can be suppressed. Furthermore, cell population of high concentration retinal pigment epithelial cells can be extremely efficiently obtained in large amounts by a simple and easy operation in a short time by the above-mentioned purification step. In addition, according to the production method of the present invention, retinal pigment epithelial cells can be adhered to each other to form a sheet-like structure. Therefore, a sheet of retinal pigment epithelial cells can be produced by the production method of the present invention. The sheet of retinal pigment epithelial cells is useful as a cell population to be used as a cell transplantation therapeutic drug for the treatment of retinal diseases, as described in detail below.

The retinal pigment epithelial cells produced as mentioned above can also be subjected to a further amplification culture. The amplification culture can be performed by, similar to in the aforementioned method, seeding retinal pigment epithelial cells on an incubator coated with laminin or a fragment thereof to allow adhesion of the cells to laminin or a fragment thereof, and conducting adhesion culture. Such passage and amplification culture select only the cells capable of specifically adhering to laminin or a fragment thereof to be the substrate are selected. As a result, since a monolayer structure of dominant retinal pigment epithelial cells are stably maintained, and the cells contained in the differentiation-induced retinal pigment epithelial cells, which could not be induced to differentiate, can be relatively reduced, it can also be used as a further purification method of retinal pigment epithelial cells.

The concentration of the retinal pigment epithelial cells to be seeded is not particularly limited as long as uniform adhesion culture of retinal pigment epithelial cells is possible. For example, when a 10 cm dish is used, it is $1 \times 10^5$-$1 \times 10^8$ cells, preferably $2 \times 10^6$-$5 \times 10^7$ cells, more preferably $5 \times 10^5$-$1 \times 10^7$ cells, per 1 dish.

Laminin or a fragment thereof, and a coating method to a culture substrate in the amplification culture are the same as those mentioned above, and so is a preferable embodiment.

As the culture medium, the aforementioned maintenance medium for retinal pigment epithelial cells can be used.

While the culture period is not particularly limited, after seeding of retinal pigment epithelial cells, the culture is preferably performed while exchanging the total amount of the medium with maintenance medium not less than once in 3 days for about 3 weeks. The cell culture medium after the culture is preferably subjected to a treatment similar to that in the above-mentioned step (2) (i.e., detachment from the incubator, optional dissociation treatment between cells, and filtering treatment) to further purify the retinal pigment epithelial cells. Furthermore, using the thus-obtained retinal pigment epithelial cells, culture similar to the above-mentioned amplification culture is preferably performed for about 2 weeks, and the obtained cell culture medium is subjected to a treatment similar to that in the above-mentioned step (2) again to perform further purification. As for the number of cells in a liquid that passed the filter by the above operation, for example, purity of retinal pigment epithelial cells of not less than 85%, preferably not less than 95%, more preferably not less than 99%, can be achieved.

According to the amplification method of the present invention, since retinal pigment epithelial cells are rapidly fixed on an incubator via laminin or a fragment thereof superior in cell adhesiveness, cell loss during medium exchange can be suppressed, and deformation of cell form due to passage can be suppressed, the maintenance culture and culture growth of retinal pigment epithelial cells can be performed stably. According to the amplification method of the present invention, moreover, a membranous retinal pigment epithelial cell group can also be utilized directly or in the form of a suspension which is separation-recovered from the culture substrate for fixing to a new substrate or supporting material (biodegradable, porous, mesh structure and the like) to be formed into a shape suitable for the affected part to which the cells are transplanted, and utilized as a therapeutic drug for retinal diseases shown below.

2. Retinal Pigment Epithelial Cell

The retinal pigment epithelial cells obtained by the purification method or production method of the present invention have high purity and have superior property whether they are used as cells alone or as a sheet.

3. Therapeutic Drug for Retinal Diseases

The retinal pigment epithelial cells obtained by the purification method or production method of the present invention can be used as a cell transplantation therapeutic drug to be transplanted in the formulated form of a suspension or sheet to living organisms for the treatment of retinal diseases. Retinal disease is an ophthalmic disease relating to the retina and also includes complications with other diseases such as diabetes and the like.

4. Toxicity, Efficacy Evaluation Drug

The retinal pigment epithelial cells produced by the amplification method or production method of the present invention can be utilized as a normal or disease model cell for screening for therapeutic drugs for retinal diseases and therapeutic drug for diseases of other complications such as efficacy evaluation diabetes and the like, or prophylactic drug thereof, safety test of chemical substances and the like, stress test, toxicity test, side effect test, infection/contamination test. On the other hand, they can also be utilized for toxicity study, toxicity test and the like of phototoxicity unique to retinal cells, retinal excitotoxicity and the like. The evaluation method thereof includes stimulation, toxicity tests such as apoptosis evaluation and the like, as well as tests for evaluation of influence on normal differentiation from progenitor cell into retinal pigment epithelial cell and visual cell (expressed protein analysis and phagocytic capacity test by RT-PCR of various gene markers, ELISA of cytokine and the like), toxicity test of phototoxicity and the like, retinal electric potential and transepithelial impedance on visual function, cell injury test caused by autoimmune reaction and the like. As a cell material for these tests, not only retinal pigment epithelial cells but also progenitor cells thereof can be used and, for example, a plate on which cells are adhered by seeding, a cell suspension, a sheet or compact thereof can be provided. They can be used as an extrapolation test of human and animal tests.

The contents disclosed in any publication cited in the present specification, including patents and patent applications, are hereby incorporated in their entireties by reference, to the extent that they have been disclosed herein.

The present invention is explained in more detail in the following by referring to Examples, which are not to be construed as limitative.

EXAMPLES

Study Example 1 Production of RPE Cell Derived from iPS Cell

Reagents differentiation induction basic medium (GMEM medium (Invitrogen), KSR (Invitrogen), 0.1 mM MEM non-essential amino acid solution (Invitrogen), 1 mM pyruvic acid sodium (SIGMA), 0.1 M 2-mercaptoethanol (Wako Pure Chemical Industries, Ltd.), 100 U/ml penicillin-100 µg/ml streptomycin (Invitrogen))

primary differentiation induction medium (differentiation induction basic medium containing 20% KSR, 10 µM Y-27632 (Wako Pure Chemical Industries, Ltd.), 5 µM SB431542 (SIGMA), 3 µM CKI-7(SIGMA))

secondary differentiation induction medium (differentiation induction basic medium containing 15% KSR, 10 µM Y-27632 (Wako Pure Chemical Industries, Ltd.), 5 µM SB431542 (SIGMA), 3 µM CKI-7(SIGMA))

tertiary differentiation induction medium (differentiation induction basic medium containing 10% KSR, 10 µM Y-27632 (Wako Pure Chemical Industries, Ltd.), 5 µM SB431542 (SIGMA), 3 µM CKI-7(SIGMA))

quaternary differentiation induction medium (differentiation induction basic medium containing 10% KSR)

RPE maintenance medium (67% DMEM low glucose (SIGMA), 29% F12 (SIGMA), 1.9 mM L-glutamine (Invitrogen), 1.9% B-27 supplement (Invitrogen), 96 U/mL penicillin sodium, 96 µg/mL streptomycin sulfate)

Production of Retinal Pigment Epithelial Cell (Differentiation Induction)

iPS cells (1120C7, provided by Kyoto University) derived from human peripheral blood (mononuclear cell) were seeded in a laminin-coated culture dish (manufactured by Sumitomo Bakelite Co., Ltd.) at $9 \times 10^6$ cells/9 cm dish. The laminin-coated culture dish was produced by coating a 9 cm culture dish (BD FALCON) with a 0.5 µg/cm$^2$ aqueous solution of laminin-511 E8 fragment (protein disclosed in Example (3) of WO 2011043405. (manufactured by Nippi (iMatrix-511, NIP-8920-02))) at 37° C. for not less than 1 hr. iPS cells rapidly adhered on the culture dish, and formation of floating aggregate was not confirmed.

With the first day of culture as Day 0, the total amount of the medium was exchanged every day from the start of the culture (Day 1) to around Day 40 when pigment cell was confirmed. The composition of the medium was changed in stages as shown below. That is, the primary differentiation induction medium (20% KSR) was used for Day 1-4, the secondary differentiation induction medium (15% KSR) was used for Day 5-8, the tertiary differentiation induction medium (10% KSR) was used for Day 9-12, and the quaternary differentiation induction medium (10% KSR) was used from Day 13 to around Day 40 when pigment cells are confirmed.

After around Day 40 when pigment cells were confirmed, the total amount of the medium was exchanged with RPE maintenance medium up to Day 47 at not less than once per 3 days. As the culture proceeded, the cell pigment became darker, and on Day 47, many cell groups containing dark pigments were observed. On Day 47, a cell population containing pigment cells was recovered.

Using laminin-511 E8 fragment as a coating agent, seeded iPS cells rapidly adhered to the culture dish at a high density, and stably maintained an adhesion state even during culture period in a differentiation induction medium. Therefore, the cell loss could be suppressed low even when the total amount of medium was repeatedly exchanged. Furthermore, the rate of generation of pigment cells was drastically improved and the differentiation induction efficiency was markedly improved as compared to when the iPS cells were seeded on an incubator coated with collagen.

Study Example 2 Production of RPE Cell (Other iPS Cell)

By a method similar to that of Study Example 1 except that iPS cells (201B7, provide by Kyoto University) derived from human skin (fibroblast) were used instead of iPS cells (1120C7, provide by Kyoto University) derived from human peripheral blood (mononuclear cell) were used, pigment cells were obtained.

As a result, like Study Example 1, the rate of generation of pigment cells relative to the seeded iPS cells was drastically improved and the differentiation induction efficiency was markedly improved.

Example 1

Purification and Amplification of RPE Cell Derived from iPS Cell

The cell population containing pigment cells on Day 47, which underwent adhesion culture in the culture dish (FIG. 3) in Study Example 1 and Study Example 2, was treated with 0.01% Trypsin-0.53 mM EDTA and cell aggregates were detached from the culture dish. Then, adhesion between the cells was detached by mild pipetting. Protease liquid and residual impurities thereof in the cell mixture were removed together with the supernatant by centrifugation, then, unnecessary cells were separated by filter filtration separation through a cell strainer (DB Falcon Cell Strainer 40 µm Nylon), and a cell population containing RPE cells was recovered (Day 48).

The obtained cells were seeded in RPE maintenance medium described in Study Example 1 in the same 5 culture dishes coated with laminin-511 E8 as in Study Example 1 at $9 \times 10^6$ cells/9 cm dish, and standing culture was performed until around Day 50 when adhesion of the RPE cell colony was confirmed.

From Day 51 to Day 71, the total amount of the medium was exchanged with RPE maintenance medium not less than once in 3 days for 3 weeks, then subjected to filtration separation using a filter (purification), seeded in each of the same 5 culture dishes coated with laminin-511 E8, and similarly cultured for 2 weeks. As a result, retinal pigment epithelial cells were amplified to the yield of 25 dishes (10 cm dish) from any cell populations of Study Example 1 and Study Example 2. The purity (n=4) of the obtained cell populations was 96.4%, 100%, 98.6% or 99.6%.

As one example, the purity calculation data of a dish with 98.6% purity is shown.

TABLE 1

| | purity calculation data of RPE cell with 98.6% purity | | | | | | | |
|---|---|---|---|---|---|---|---|---|
| | positive cell | | | | negative cell | | | |
| | | | | pigment negativity | | | | |
| visual field | pigment positive | Bestrophin positive | Pax6 positive | Bestrophin, Pax6 both positive | Bestrophin, Pax6 both negative | total positive cells | total cells | purity (%) |
| 1 | 11 | 0 | 0 | 6 | 0 | 17 | 17 | 98.6 |
| 2 | 176 | 5 | 33 | 30 | 4 | 244 | 248 | |
| 3 | 88 | 0 | 0 | 14 | 1 | 102 | 103 | |

As for purity, immunostaining for Pax6, Bestrphin and Mitf was performed, and when either was stained, the cell was judged to be an RPE cell. When fluorescence was not observed, the presence or absence of intracellular melanin pigment was examined, and the cell was judged to be an RPE cell based on the confirmation of the pigment (since some pigments inhibit fluorescence observation, cell was judged to be RPE cell in the presence of pigment even when fluorescence was not observed). The purity was determined by a method including adding each as positive cells.

This Example afforded similar results even when iPS cells of a different line (201B7) were used. In addition, even when purification similar to this Example was performed using a filter having a pore size of 70 µm or 20 µm, similarly highly pure RPE cells were obtained.

Comparative Example 1

By a method similar to that of Study Example 1 except that, in the differentiation induction step of Study Example 1, floating culture was performed using a non-adhesive culture dish (Nunc) treated with MPC (2-methacryloxyl-ethyl phosphoryl choline) instead of adhesion culture using a culture dish coated with laminin-511 E8 (BD FALCON), a differentiation induction step was performed.

As a result, almost all pigment cells were lost during medium exchange in the differentiation induction step, pigment cell could not be recovered on Day 47.

Comparative Example 2

By a method similar to that in Study Example 1 except that, in the differentiation induction step of Study Example 1, adhesion culture was performed using a culture dish coated with poly-D lysine and gelatin instead of a culture dish coated with laminin-511 E8, differentiation induction was performed.

The adhesiveness of the cell to the poly-D lysine/gelatin-coated culture dish was weak as compared to the laminin- 511 E8-coated culture dish, and the cells were easily lost during medium exchange. Therefore, the rate of the pigment cells on Day 47 after the start of the culture was not more than 1/20 of Study Example 1 by visual observation of the number of pigment cells relative to the total cells in the culture dish, and differentiation induction efficiency was also m markedly low.

(Evaluation 1) Expression of RPE Cell Marker

The pigment cells obtained in Study Examples 1 and 2, and Example 1 were subjected to RT-PCR analysis using primers having the following sequences, according to the method described in Journal of Cell Science 2009 Sep. 1 122 3169-79. As a result, expression of RPE cell specific genes (RPE65, CRALBP, MERTK, BEST1) was found, similar to commercially available human RPE cell lines, thus confirming RPE cells.

```
RPE65-F
                                      (SEQ ID NO: 1)
TCC CCA ATA CAA CTG CCA CT

RPE65-R
                                      (SEQ ID NO: 2)
CCT TGG CAT TCA GAA TCA GG

CRALBP-F
                                      (SEQ ID NO: 3)
GAG GGT GCA AGA GAA GGA CA

CRALBP-R
                                      (SEQ ID NO: 4)
TGC AGA AGC CAT TGA TTT GA

MERTK-F
                                      (SEQ ID NO: 5)
TCC TTG GCC ATC AGA AAA AG

MERTK-R
                                      (SEQ ID NO: 6)
CAT TTG GGT GGC TGA AGT CT

BEST1-F
                                      (SEQ ID NO: 7)
TAG AAC CAT CAG CGC CGT C

BEST1-R
                                      (SEQ ID NO: 8)
TGA GTG TAG TGT GTA TGT TGG
```

Figure 2:
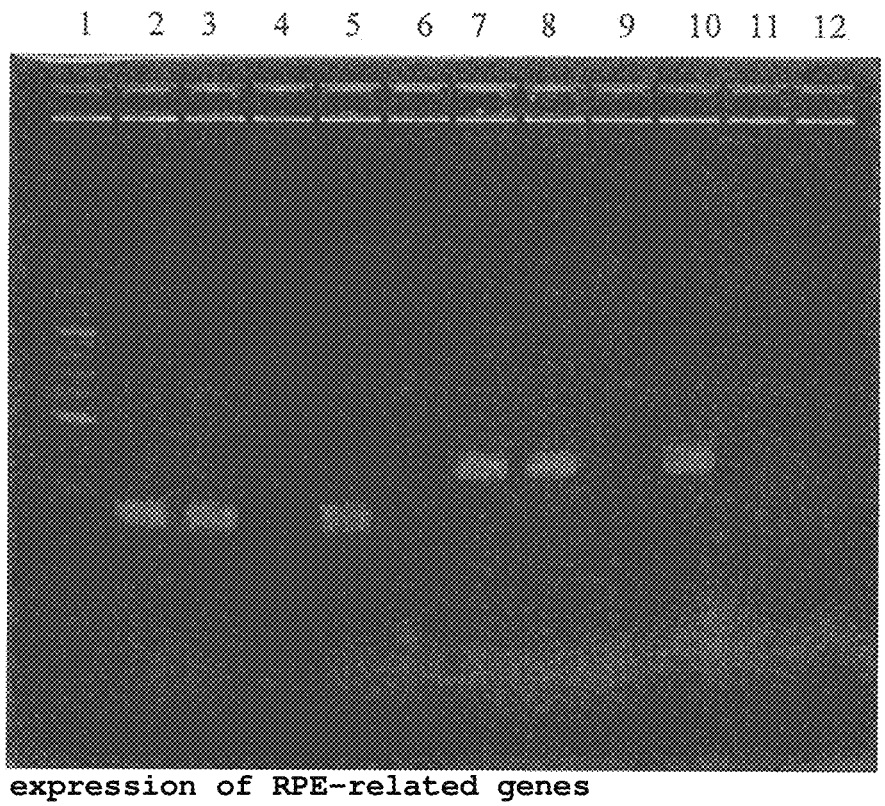
FIG. 2 shows expression of RPE-related genes by RPE cells induced from human iPS cells (201B7 and 1120C7).

This Example afforded similar results even when iPS cells of a different line (201B7) were used. As a representative Example, the results obtained using RPE65 are shown in FIG. 2.

(Evaluation 2) Cytokine Secretional Capacity

The pigment cells obtained in Study Examples 1 and 2, and Example 1 were detected for the production amount of PEDF by ELISA according to the method described in IOVS. 2006 47 612-3624. As a result, it was confirmed that they similarly had cytokine secretional capacity like the RPE cells of adult retina (Table 2).

TABLE 2

| PEDF secretion amount | | | | | |
|---|---|---|---|---|---|
| days after | concentration (ng/mL) | | | | |
| passage | Example 1 | Example 2 | Example 3 | mean | standard error |
| 7 | 945.2 | 998.8 | 993.3 | 979.1 | 17.0 |
| 10 | 1266.1 | 1263.1 | 1288.0 | 1272.4 | 7.9 |
| 12 | 1574.3 | 1567.0 | 1616.3 | 1585.8 | 15.4 |
| 14 | 1542.0 | 1622.4 | 1524.3 | 1562.9 | 30.2 |
| 17 | 1621.2 | 1533.5 | 1482.9 | 1545.8 | 40.4 |
| 19 | 1727.7 | 1752.7 | 1842.8 | 1774.4 | 35.0 |
| 21 | 1504.8 | 1581.0 | 1570.6 | 1552.1 | 23.8 |

This Example afforded similar results even when iPS cells of a different line (201B7) were used.

(Evaluation 3) Phagocytic Capacity

The pigment cells obtained in Study Examples 1 and 2, and Example 1 were analyzed for the phagocytic capacity according to the method described in J Cell Sci. 1993 104 37-49, and using FLUOSPHERES™ fluorescent microsphere (Invitrogen, F13081). As a result, it was confirmed that the cells had phagocytic capacity of the same level as commercially available human RPE cell line. This Evaluation afforded similar results even when iPS cells of a different line (201B7) were used. In addition, similar results were obtained even when the phagocytic capacity was analyzed using iPS cells of a different line (201B7) and PHRODO™ GREEN *E. COLI* BIOPARTICLES™ Conjugate for Phagocytosis (Molecular Probes, P35366), according to the method described in The Lancet 2012 379 713-720.

(Evaluation 4) Analysis of Expression of Cell Population Before and after Purification The cell aggregates detached in Study Examples 1 and 2 were passed through a cell strainer (DB Falcon Cell Strainer 40 ul Nylon), and a cell population remaining on the filter and a cell population containing separated retina epithelial cell group were each subjected to gene expression analysis and evaluated for the cell type and differentiation stage.

Figure 4:
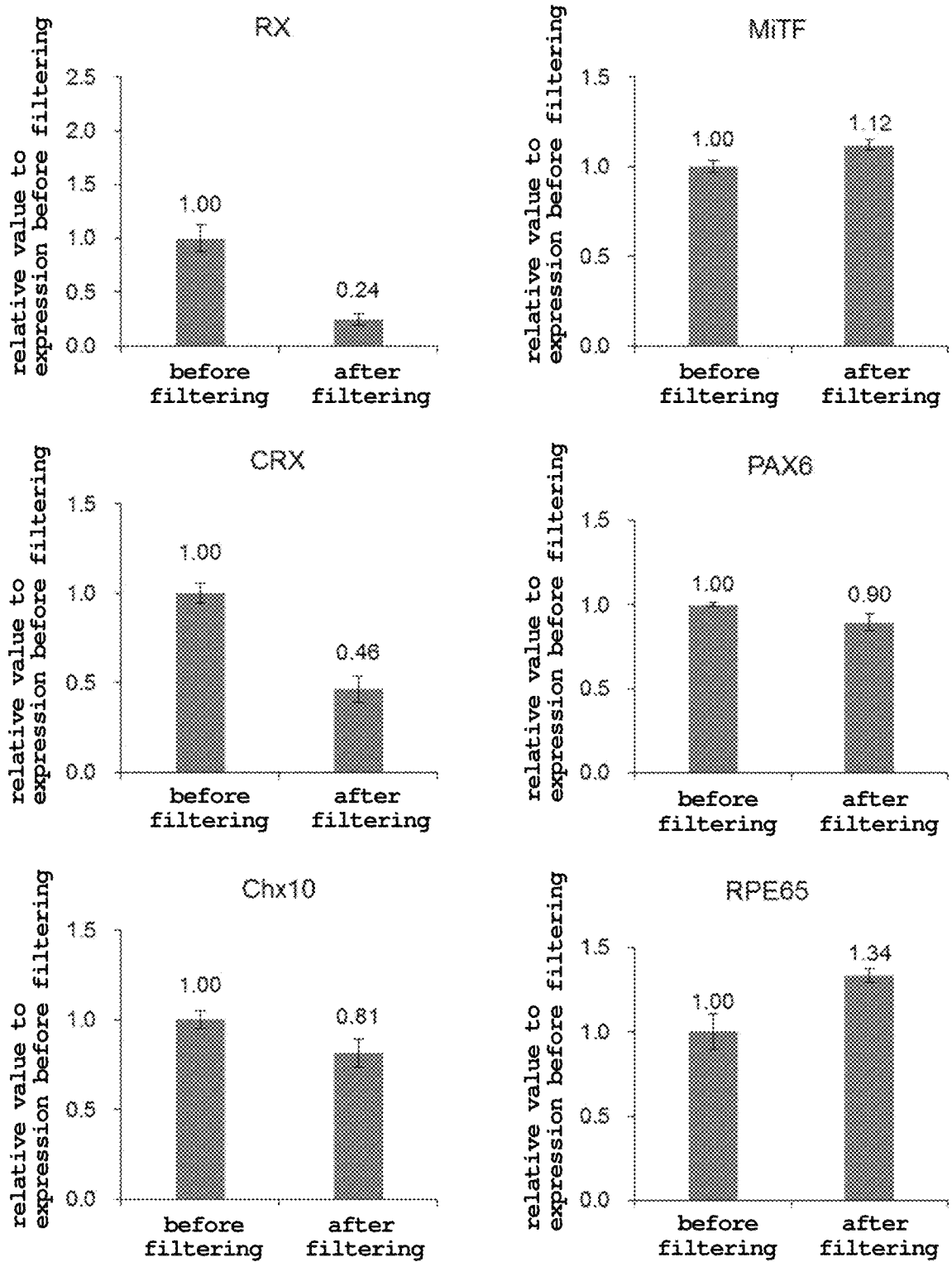
FIG. 4 shows expression of retinal pigment epithelial cell marker genes, progenitor cell and nerve cell marker genes before and after purification with a filter. The values show relative value±standard deviation (n=1, 3 repeat measurements) with the expression level before filtering as 1.

To be specific, expression of specific genes was detected by the quantification RT-PCR method and the effect of the separation of retinal pigment epithelial cells was evaluated by the filter filtration method. RNA was extracted from the cells separated on and under the filter according to a conventional method (RNeasy Micro Kit, 79254, QIAGEN), and cDNA was synthesized using the extracted RNA as a template (SuperScript III reverse transcriptase kit, 18080-044, Invitrogen, 0.5 μg/μL Oligo (dT)12-18 Primer, invitrogen, 18418-012, invitrogen, 10 mM dNTP Mix, 18427-013, invitrogen). Using the synthesized cDNA as a template, the expression of the object gene was detected under PCR conditions of 1) 95° C. for 20 seconds, 2) 95° C. for 1 second, 3) 60° C. for 20 seconds (40 cycles of 2)-3)) (20×TaqMan (registered trade mark) Gene Expression Assay, Applied Biosystems, 2×TaqMan (registered trade mark) Fast Advanced Master Mix, 4444557, Applied Biosystems). Using GAPDH as the internal standard, the expression level was normalized, the relative value was calculated by the comparison Ct method with the expression level of the gene of interest before filter filtration as 1 (FIG. 4). The primer sequences used for gene amplification are shown below.

20×TaqMan (registered trade mark) Gene Expression Assay (RAX(Rx)) (Applied Biosystems) Hs00429459_m1
20×TaqMan(registered trade mark) Gene Expression Assay (Pax6) (Applied Biosystems) Hs00240871_m1
20×TaqMan(registered trade mark) Gene Expression Assay (MITF) (Applied Biosystems) Hs01117294_m1
20×TaqMan(registered trade mark) Gene Expression Assay (RPE65) (Applied Biosystems) Hs01071462_m1
20×TaqMan(registered trade mark) Gene Expression Assay (CRX) (Applied Biosystems) Hs00230899_m1

20×TaqMan(registered trade mark) Gene Expression Assay (VSX2(Chx10)) (Applied Biosystems) Hs1584047_m1
20×TaqMan(registered trade mark) Gene Expression Assay (GAPDH) (Applied Biosystems) Hs02758991_g1

As a result, it could be confirmed that retinal pigment epithelial cell marker (RPE65) and its progenitor cell marker Mitf (pigment epithelium cell, progenitor cell) were highly expressed under the filter, and the markers expressed in the very initial stages of differentiation induction such as Pax6 (progenitor cell), Rx (retina progenitor cell), Crx (visual cell progenitor cell), Chx10 (bipolar cell) and the like and visual cell and nerve cell markers other than the object cells were highly expressed on the filter. Therefrom it is considered that the use of the purification method at the end-point of a differentiation induction step is suitable as a method of efficiently separating the retinal pigment epithelial cells.

INDUSTRIAL APPLICABILITY

According to the purification method of the present invention, retinal pigment epithelial cells induced from pluripotent stem cells can be purified conveniently in a high yield. According to the production method using the purification method of the present invention, retinal pigment epithelial cells can be produced efficiently and at high purity by a simple and easy method using a culture substrate coated with laminin or a fragment thereof. The production method of the present invention is superior in the differentiation induction efficiency and can purify retinal pigment epithelial cells by a simple and easy operation, and can produce retinal pigment epithelial cells in a high yield by suppressing cell loss during the step. The retinal pigment epithelial cells produced by the method of the present invention are useful not only for the treatment of retinal diseases but also as a production or preparation method of normal and disease model cells.

This application is based on a patent application No. 2013-212345 filed in Japan (filing date: Oct. 9, 2013), the contents of which are incorporated in full herein.

The invention claimed is:

1. A method of purifying a retinal pigment epithelial cell, comprising
   (1) a step of inducing differentiation of pluripotent stem cells into a cell population on laminin-511E8 fragment, wherein the cell population contains (a) retinal pigment epithelial cells without forming a mixture with a jelly-like substance and (b) other visual cells contained in the jelly-like substance,
   (2) a step of recovering the entire cell population containing (a) and (b) obtained in step (1) by treating it with a cell separating solution,
   (3) a step of dissociating adhesion between retinal pigment epithelial cells contained in the entire cell population containing (a) and (b) obtained in step (2),
   (4) a step of introducing the entire cell population containing (a) and (b) obtained in step (3) on a filter, and
   (5) a step of obtaining retinal pigment epithelial cells that passed the filter, wherein the filter has a pore size of 15-100 μm.

2. The method according to claim 1, wherein the step of dissociating adhesion between retinal pigment epithelial cells is reciprocating pipetting several times.

3. The method according to claim 1, wherein the cell separating solution comprises trypsin.

4. The method according to claim 1, wherein the filter has a pore size of 20-70 μm.

5. The method according to claim 1, wherein step (3) further comprises, after dissociating adhesion between retinal pigment epithelial cells contained in the cell population, removing the cell separating solution and residual impurities thereof and matrix components in the cell population together with supernatant by centrifugation.

6. A method of producing a retinal pigment epithelial cell from a pluripotent stem cell, comprising
   (1) a step of inducing differentiation of pluripotent stem cells into a cell population on laminin-511E8 fragment, wherein the cell population contains (a) retinal pigment epithelial cells without forming a mixture with a jelly-like substance and (b) other visual cells contained in the jelly-like substance,
   (2) a step of recovering the entire cell population containing (a) and (b) obtained in step (1) by treating it with a cell separating solution,
   (3) a step of dissociating adhesion between retinal pigment epithelial cells contained in the entire cell population containing (a) and (b) obtained in step (2), and
   (4) a step of introducing the entire cell population containing (a) and (b) obtained in step (3) on a filter to obtain retinal pigment epithelial cells that passed the filter, wherein the filter has a pore size of 15-100 μm.

7. The method according to claim 6, wherein the step of dissociating adhesion between retinal pigment epithelial cells is reciprocating pipetting several times.

8. The method according to claim 6, wherein the cell separating solution comprises trypsin.

9. The method according to claim 6, wherein the filter has a pore size of 20-70 μm.

10. The method according to claim 6, wherein step (3) further comprises, after dissociating adhesion between retinal pigment epithelial cells contained in the cell population, removing the cell separating solution and residual impurities thereof and matrix components in the cell population together with supernatant by centrifugation.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
tccccaatac aactgccact                                                  20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
ccttggcatt cagaatcagg                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
gagggtgcaa gagaaggaca                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
tgcagaagcc attgatttga                                                  20

<210> SEQ ID NO 5
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 5
tccttggcca tcagaaaaag                                            20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
catttgggtg gctgaagtct                                            20

<210> SEQ ID NO 7
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 7
tagaaccatc agcgccgtc                                             19

<210> SEQ ID NO 8
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 8
tgagtgtagt gtgtatgttg g                                          21
```